United States Patent [19]
Gillig et al.

[11] Patent Number: 5,559,228
[45] Date of Patent: Sep. 24, 1996

[54] SYNTHESIS OF BISINDOLYLMALEIMIDES

[75] Inventors: James R. Gillig; Michael R. Jirousek, both of Indianapolis, Ind.

[73] Assignee: Eli Lilly and Company, Indianapolis, Ind.

[21] Appl. No.: 413,311

[22] Filed: Mar. 30, 1995

[51] Int. Cl.$^6$ ............. C07D 487/08; C07D 487/06; C07D 498/16; C07D 498/18
[52] U.S. Cl. ............. 540/460; 540/469; 540/472
[58] Field of Search .................. 540/460, 469, 540/472

[56] References Cited

U.S. PATENT DOCUMENTS

| | | | |
|---|---|---|---|
| 5,057,614 | 10/1991 | Davis et al. | 548/466 |
| 5,292,747 | 3/1994 | Davis et al. | 514/285 |
| 5,380,746 | 1/1995 | Barth et al. | 514/414 |

FOREIGN PATENT DOCUMENTS

| | | | |
|---|---|---|---|
| 3914764A1 | 11/1990 | Denmark | 403/14 |
| WO91/13071 | 9/1991 | European Pat. Off. | 403/14 |
| 0540956A1 | 10/1992 | European Pat. Off. | 471/14 |
| 0397060A2 | 5/0490 | Germany | 403/14 |
| WO91/13070 | 9/1991 | Germany | 403/04 |
| WO94/07895 | 4/1494 | WIPO | C07D 487/22 |

OTHER PUBLICATIONS

Harris, et al., *Tetrahedron Letters*, 34:51, 8361–8364 (1993).
McMurry, et al., *J. Org. Chem.*, 54, 3748–3749 (1989).
Gribble, et al., *J. Org. Chem.*, 57, 3636–3642 (1992).
Bergman, et al., *Tetrahedron Letters*, 28:38, 4441–4444 (1987).
McMurry, et al., *American Chemical Society*, 105, 1660–1661 (1983).
Chrisholm et al., *J. Amer. Chem. Soc.*, 111, 2324–2325.
Fürster, et al., *J. Org. Chem.*, 59, 5215–5229 (1994).
McMurry, *Chem. Rev.*, 89, 1513–1524 (1989).
Clerici, et al., *Tetrahedron Letters*, 22, 1043–1046 (1981).
Baumstark, et al., *J. Org. Chem.*, 43:18, 3609–3611 (1978).
Mukaiyama, et al., *Chemistry Letters*, 1041–1044 (1973).
Ledon, et al., *Tetrahedron Letters*, No. 2, 173–176.
Coe, et al., *J. Chem Soc. Perkin Trans. I*, 475–477 (1986).
Nakayama, et al., *J. Chem. Soc., Chem. Commun.*, 1072–1073 (1987).
Chen, et al., *Synthesis*, 182–184 (Mar. 1989).
Dams, et al., *J. Org. Chem.*, 47, 248–259 (1982).

*Primary Examiner*—Mukund J. Shah
*Assistant Examiner*—Anthony P. Bottino
*Attorney, Agent, or Firm*—Steven P. Caltrider; David E. Boone

[57] ABSTRACT

The present invention provides an efficient process of reacting a bis-indolyl acid of the Formula (II):

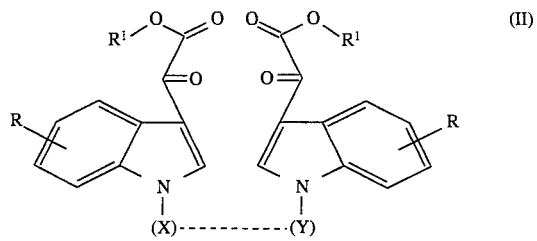

wherein $R^1$ is a hydrogen or $C_1$–$C_4$ alkyl and R, X, and Y are optional substitutions; to produce a bis-indolyloxallic acid of the Formula (III):

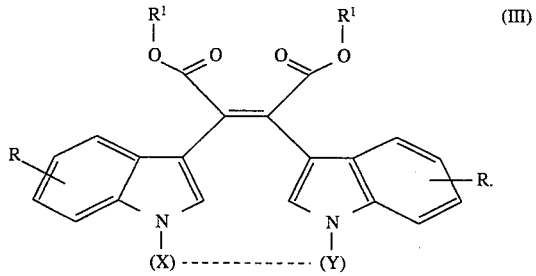

Compounds of the Formula (III) are readily converted to the bis-indolylmaleimides.

4 Claims, No Drawings

SYNTHESIS OF BISINDOLYLMALEIMIDES

BACKGROUND OF THE INVENTION

Therapeutically, an antagonist that possesses both kinase selectivity for protein kinase C (PKC) and PKC isozyme selectivity is a potentially useful pharmacological agent. Hartenstein, J. H. et al., "Perspectives in Medicinal Chemistry," 99–118 (1993), VCH Publishers, New York. Such an antagonist of protein kinase C would be useful in treating disease states in which PKC has been implicated. Lester, D. S., et al., "Protein Kinase C: Current concepts and Future Perspectives", Ellis Horwood New York (1992). Specific isozymes of protein kinase C have been implicated in cancer (Ahmed, et al., *Mol. Pharma.*, 43, 858–86 (1993), CNS diseases such as Alzheimer's (Demaerschalck, et al., *Biochem. Biophys. Acta.* 1181, 214–218 (1993)), cardiovascular disease (Natarajan et al. *Mol. Cell. Endo.*, 101, 59–66 (1994)) and diabetic complications (King, et al., *Proc. Nat. Acad. Sciences* (USA), 88:22, 11059–63 (1992)).

Recently, a class of compounds, referred to herein as bis-indolylmaleimides, have been identified as potent and effective inhibitors of PKC. Compounds within this class are described, for example, in Davis et al., U.S. Pat. No. 5,057,614 (1991), Barth et al., European patent Application 397 060 (1992), Schultz et al., in PCT application WO 91/13070, Barth et al., U.S. Pat. No. 5,380,746, U.S. patent application Ser. No. 08/163,060, abandoned, U.S. patent application Ser. No. 08/324,948, and U.S. patent application Ser. No. 08/316,973, abandoned. This class of compound is generally represented by Formula I:

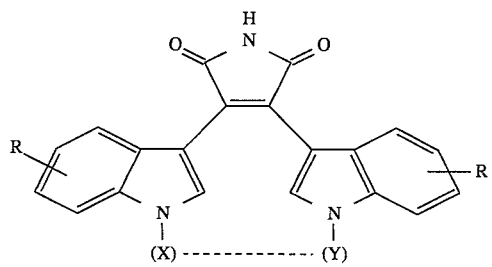

wherein X, Y and R represent optional substitutions.

The present invention provides a novel process for preparing compounds of the Formula I. More specifically, the invention provides an efficient process for reacting a bis-alpha-keto indolyl acid of the Formula II:

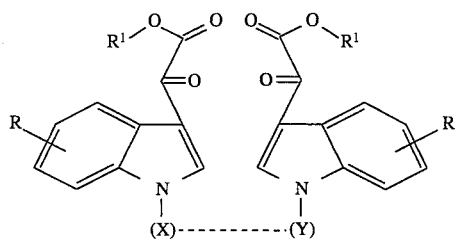

wherein $R^1$ is a hydrogen, $C_1$–$C_4$ alkyl or benzyl, and R, X, and Y are optional substitutions; to produce a novel bis-indolylmaleic acid of the Formula III:

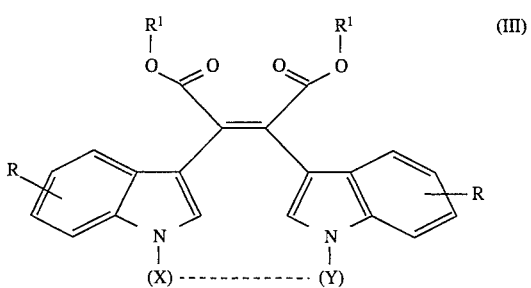

Compounds of the Formula III are readily converted to the bisindolylmaleimide of Formula I.

Reductive dimerization with ketones and aldehydes to yield olefins on treatment with low-valent titanium reagents is known in the art and generally described in J. E. McMurry, *Chem. Rev.* 89: 1513–24 (1989). The reaction is also described in J. E. McMurry et al., *J. Am, Chem. Soc.* 105:1660–61 (1982), which demonstrates keto ester cyclization under similar conditions. However, before the present invention, it was unknown that low valent titanium effectively couples alpha keto indolyl acids of the Formula II. Thus, under the conditions described herein, the compounds of Formula I may be produced in an efficient process at high yield.

SUMMARY OF THE INVENTION

The invention provides a process of preparing a bisindolylmaleic acid ester, which comprises:

Reacting a bis-indolyl acid of the Formula II:

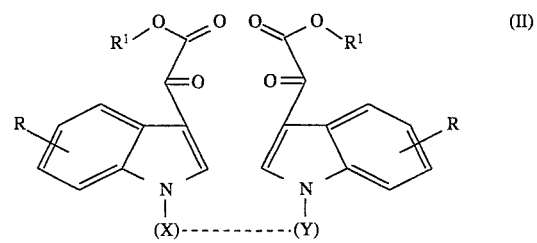

wherein $R^1$ is a hydrogen, $C_1$–$C_4$ alkyl or benzyl; and R, X, and Y are optional substitutions; in the presence of a low valent titanium reagent to form a bis-indolylmaleic acid of the Formula III:

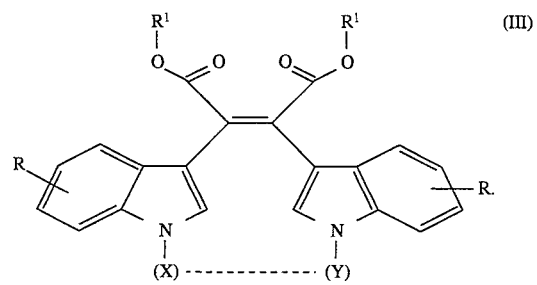

The invention further provides converting the bisindolylmaleic acid to a bis-indolylmaleimide, which comprises:

Hydrolizing the acid of Formula III to form an anhydride of the Formula IV:

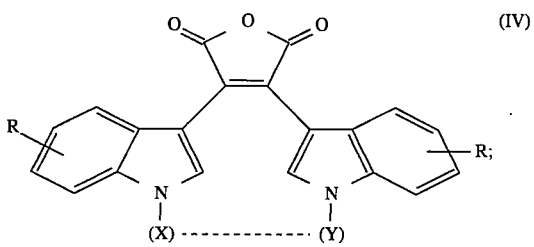

Converting the anhydride (IV) to a bis-indolyl maleimide of the Formula I.

DETAILED DESCRIPTION AND PREFERRED EMBODIMENT

For purposes of the present invention, as disclosed or claimed herein, the following terms are defined as follows.

The term "halo", as used herein, represents fluorine, chlorine, bromine, or iodine.

The term "$C_1$–$C_4$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like. A haloalkyl is one such alkyl substituted with one or more halo atoms, preferably one to three halo atoms. An example of a haloalkyl is trifluoromethyl. A $C_1$–$C_4$ alkoxy is a $C_1$–$C_4$ alkyl group covalently bonded by an —O— linkage.

The term "aryl" represents a substituted or unsubstituted phenyl or naphthyl. Aryl may be optionally substituted with one or two groups independently selected from hydroxy, carboxy, $C_1$–$C_4$ alkoxy, $C_1$–$C_4$ alkyl, haloalkyl, nitro, —$NR^4R^5$, —NHCO($C_1$–$C_4$ alkyl), —NHCO(benzyl), —NHCO(phenyl), SH, S($C_1$–$C_4$ alkyl), —OCO($C_1$–$C_4$ alkyl), —$SO_2(NR^4R^5)$, -$S0_2$($C_1$–$C_4$ alkyl), —$SO_2$(phenyl), or halo. The term aryloxy is one such aryl covalently bonded by an —O— linkage. The term $(CH_2)_m$aryl is preferably benzyl or phenyl.

The notation "--------" indicates an optional bond, i.e., X and Y are optionally bond together.

(X), (Y), and R are optional subsitutions recognized in the art as being acceptable on pharmacologically active bis-indolylmaleimides. For example, in U.S. Pat. No. 5,057,614 herein incorporated by reference, (X) and (Y) independently signify hydrogen, alkyl, aryl, aralkyl, alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylithioalkyl. Similarly, R is hydrogen, halogen, alkyl, hydroxy, alkoxy, aryloxy, haloalkyl, nitro, amino, acylamino, monoalkylamino, dialkylamino, alkylthio, alkylsulphinyl or alkylsulphonyl. Other substituents accepted in the art for these positions may be found in U.S. Pat. No. 5,380,746, herein incorporated by reference.

In a preferred embodiment, (X) and (Y) are bonded together as disclosed in U.S. patent application Ser. No. 08/316,973. Most preferably, (X) and (Y) combine to form a six through nine atom macrocycle of the Formula Ia:

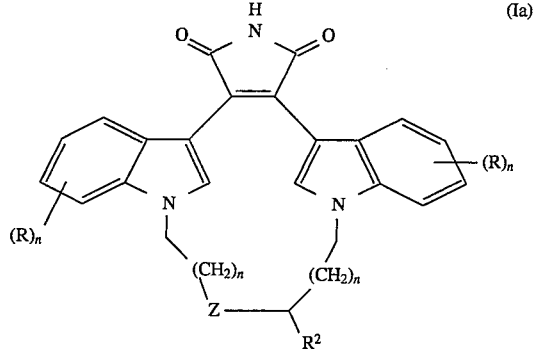

wherein:

Z is —O—, —S—, —$NR_3$—, —CONH—, or —NHCO—;

R is independently hydrogen, halo, $C_1$–$C_4$ alkyl, hydroxy, $C_1$–$C_4$ alkoxy, haloalkyl, nitro, $NR^4R^5$, or —NHCO($C_1$–$C_4$ alkyl);

$R^2$ is hydrogen, $C_1$–$C_4$ alkyl, —$(CH_2)_nC_1$–$C_4$ alkoxy, $(CH_2)_n$aryl, $(CH_2)_n$aryloxy, —$(CH_2)_n$hydroxy, —$(CH_2)_n$carboxy, —$(CH_2)_n$COO ($C_1$–$C_4$ alkyl ), —$(CH_2)_n$COO (($CH_2)_n$aryl), —$(CH_2)_n$ CO($C_1$–$C_4$ alkyl), —$(CH_2)_nNR^4R^5$, —$(CH_2)NH(CF_3)$, —$(CH_2)N(CF_3)$ $(CH_3)$, $(CH_2)_n(NR^4R^5)$ $(OR^4)$, —$(CH_2)_nNH(CH_2)_n$aryl, —$(CH_2)_nNH$ $(CH_2)_n$pyridyl, —$(CH_2)_nCONH((CH_2)_m$aryl), —$(CH_2)_nCONH(C_1$–$C_4$ alkyl), —$(CH_2)_nNHCO(C_1$–$C_4$ alkyl), —$(CH_2)_nNHCO(CH_2)_n$aryl, —$(CH_2)_nOCONH(C_1$–$C_4$ alkyl), —$(CH_2)_nOCONH(CH_2)_n$aryl, —$(CH_2)_nNHCOO$(alkyl), —$(CH_2)_nNHCOO$(benzyl), —$(CH_2)_nNHSO_2$ ($C_1$–$C_4$ alkyl), —$(CH_2)_nNHSO_2$ $(CH_2)_m$aryl, —$(CH_2)_n$CN, —$(CH_2)_n$SH, —$(CH_2)_nS(C_1$–$C_4$ alkyl), —$(CH_2)_nS$(aryl), —$(CH_2)_nSO_2$ $(NR^4R^5)$, —$(CH_2)_nSO_2(C_1$–$C_4$ alkyl), or —$(CH_2)_nSO(C_1$–$C_4$ alkyl);

$R^3$ is hydrogen, $(CH_2)_n$aryl or $C_1$–$C_4$ alkyl;

$R^4$ and $R^5$ are independently hydrogen, methyl, phenyl, benzyl, or combine to the nitrogen to which they are bonded to form a saturated or unsaturated 5 or 6 membered ring; and n is independently 1, 2 or 3.

The most preferred compounds of the Formula Ia are those wherein R is hydrogen; $R^2$ is —$CH_2NR^4R^5$; n is 1; and $R^4$ and $R^5$ are methyl.

Compounds of the Formula Ia are disclosed in U.S. patent application Ser. No. 08/316,973.

As noted above, the invention provides a process of preparing a bis-indolylmaleic acid, which comprises:

Reacting a bis-indolyl acid of the Formula II:

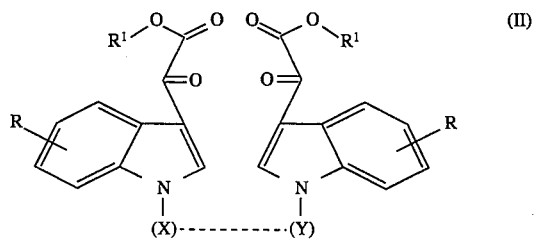

wherein $R^1$ is a hydrogen, $C_1$–$C_4$ alkyl or benzyl; and R, X, and Y are optional substitutions; in the presence of a low valent titanium reagent to form a bis-indolylmaleic acid of the Formula III:

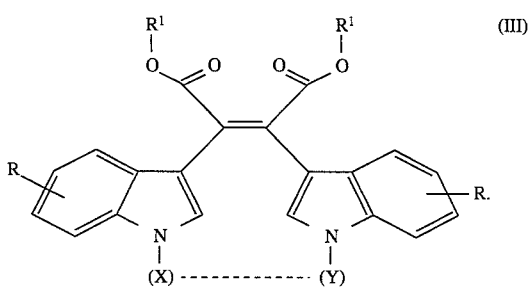

The invention further provides converting the bisindolyl-maleic acid to a bis-indolylmaleimide, which comprises:

Hydrolizing the compound of Formula III to form an anhydride of the Formula IV:

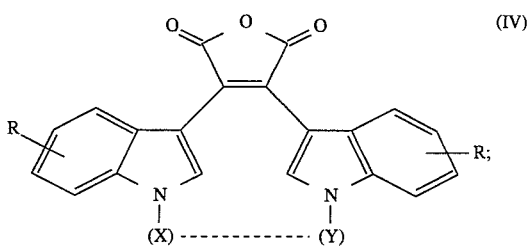

and

Converting the anhydride (IV) to a bis-indolyl maleimide of the Formula I.

The preparation of a bis-indolyl acid of the Formula II is carried out as follows:

Scheme 1

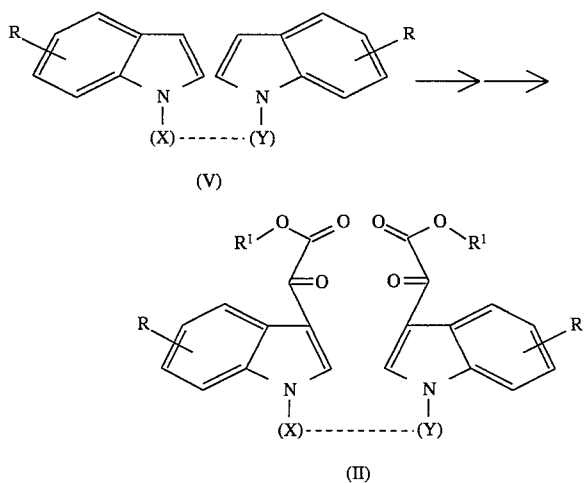

In the above Scheme 1, $R^1$, R, X and Y are the same as previously defined. Preferably, $R^1$ is a $C_1$–$C_4$ alkyl. Formation of the indolyl acid of the Formula II is carried out under conditions recognized in the art and described in G. W. Gibble et al., *J. Org. Chem*, 57:3636–42 (1992); M. Giua et al., *Chim. Ital.* 54, 593 (1924); M. E. Speeter et al., *J. Am. Chem. Soc.* 76: 6208 (1954); and A. G. Gudmundson et al., *J. Org. Chem.* 23: 1171 (1958).

Preferably, a compound of the Formula V is reacted dropwise with about two to twenty equivelents of oxalyl chloride at –30° C. to ambient temperature in an inert solvent, such as ether or THF, to form 3-indolylglyoxylyl chloride. The reaction is quenched with methanol. The product is precipitated by the addition of acid, collected, resuspended and neutralized by the addition of base to form the compound of Formula II.

The compound of Formula II is then reacted in a novel process in accordance with Scheme 2.

Scheme 2

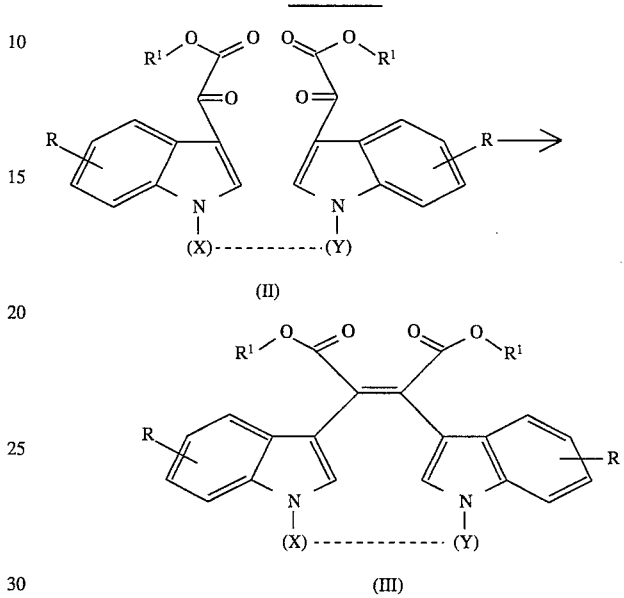

Scheme 2 describes the reaction of a compound of the Formula II with a low-valent titanium reagent to form a compound of the Formula III. The reaction is carried out in one or more inert solvents recognized to one skilled in the art. For example, the reaction may be carried out in one or more of the following solvents: ether, THF, methylene chloride, DMF, DME, or pyridine. Preferably, the solvent is DME, methylene chloride and THF.

The reaction of Scheme 2 is carried out with from about 2 to about 40 equivalents of the low-valent titanium reagent per mole of Compound II. Preferably, the reaction is carried out with 2 to 20 equivalents of the low-valent titanium reagent per mole of Compound II. The reaction is operable from –20° C to the reflux temperature of the reaction mixture. Preferably, the reaction is carried out from 0° C. to the reflux temperature. The reaction is generally complete from about 10 minutes to about 48 hours.

A low-valent titanium reagent is prepared in situ by reacting $TiCl_3$ or $TiCl_4$ with a reducing agent capable of reducing titanium to its Ti(O), Ti(I), Ti(II) oxidation state or a mixture of these oxidation states. Thus, acceptable reducing agents include $LiAlH_4$, Li, Zn—Cu, and Zn. Preferred reducing agents include Zn and Zn—Cu. Zn—Fe is also operable when added subsequent to the addition of $TiCl_3$. The preferred reducing agents are Zn and Zn—Cu. The amount of reducing agent necessary is dependent on the reducing agent selected and the reaction conditions. Generally, 15 mg to 1500 mg reducing agent per mmol $TiCl_3$, preferably 75 mg to 500 mg reducing agent per mole $TiCl_3$ are operable.

Table 1 demonstrates the reaction with various reducing agents.

TABLE I

| | Reductive Coupling using 1M TiCl$_3$ 2:1 CH$_2$Cl$_2$/THF | | |
|---|---|---|---|
| Reaction | Reducing Agent | Time (hours) | Isolated Yield |
| 1 | Zn | 16 | 35% |
| 2 | Zn—Cu | 16 | 33% |
| 3 | Zn—Fe | 16 | 8% |
| 4 | Zn | 48 | 51% |
| 5 | Zn—Cu | 48 | 33% |
| 7 | Zn | 16 | 38% |
| 8 | Zn—Cu | 16 | 48% |
| 9 | Zn—Cu | 2 | 48% |

In the above Table 1, all reactions were carried out at room temperature. Reactions 1, 2, 3, 6, and 7 were run in DME. Reaction 4 and 5 were run in 25% CH$_2$Cl$_2$ in DME. In Reaction 4 and 5, Compound II in DME/CH$_2$Cl$_2$ (4:1) was added to a stirred slurry of TiCl$_3$ and Zn over 10 hours. In reaction 6 and 7, TiCl$_3$, Compound II and Zn were suspended in DME and stirred. Table 1 demonstrates that the reducing agent employed is not critical to the present invention. One skilled in the art would recognize, by varying the reaction parameters, such as the order of addition and time of reaction, any reducing agent capable of reducing titanium to its low-valent oxidation states is operable.

The novel intermediate (III) may be isolated and purified by standard techniques including chromatography, trituration, crystallization, filtration, or a combination of these or other techniques recognized in the art.

The compound of Formula III is readily converted to the bis-indolylmaleimide of Formula I in accordance with in Scheme 3.

Scheme 3

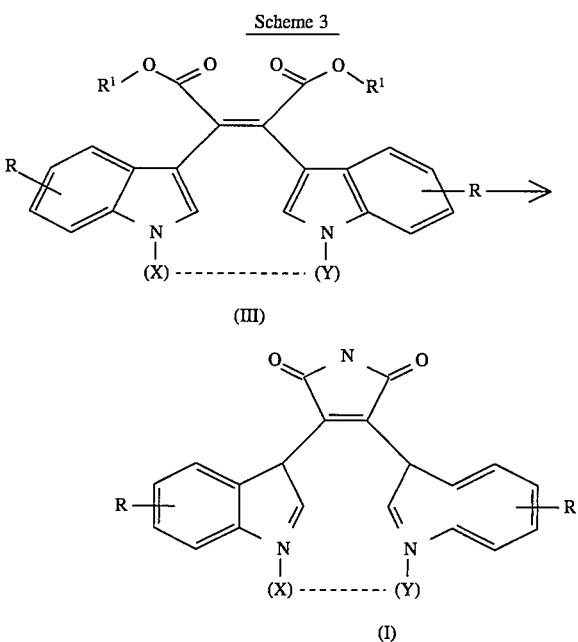

In the above scheme R$^1$, R, X and Y are the same as previously defined. The compound of the Formula III is hydrolized under strongly acidic or basic conditions to form an anhydride of the Formula IV:

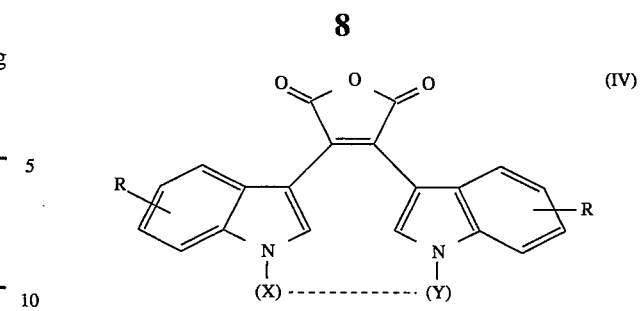

The conditions necessary to hydrolize the compound of Formula III to form the anhydride are appreciated in the art for hydrolyzing an ester. Preferably, the anhydride is formed using base, such as sodium hydroxide, in an aqueous solvent followed by acidic work-up conditions.

The anhydride of Formula IV is converted to the bisindolyl maleimide of the Formula I by techniques appreciated in the art and described in P. D. Davis et al., *Tetrahedron Lett.* 31: 5201–04 (1990) and U.S. Pat. No. 5,057,614. For example, the anhydride is reacted with an excess of hexamethyldisilazane or an ammonium salt (ammonium acetate, bromide, or chloride) and C$_1$-C$_4$ alcohol (preferably methanol) in an polar aprotic solvent such as DMF at room temperature. Preferably, the hexamethyldisilazane or an ammonium salt is reacted at a ratio greater than about 5:1 equivalents of anhydride.

As previously stated, the reaction of ketones and aldehydes to undergo a reductive dimerization to yield olefins in the presence of low-valent titanium reagents is known in the art and generally described in J. E. McMurry et al., *Chem. Rev.* 89: 1513–24 (1989). However, before the present invention, it was unknown that low valent titanium effectively couples alpha keto indolyl acids of the Formula II in high yield. Under the conditions described herein, the reaction proceeds in a chemoselective manner. The chemoselectivity of the reaction is quite surprising in view of J. E. McMurry et al., *J. Am. Chem. Soc.* 105: 1660–61 (1982), which demonstrates keto ester cyclization under similar conditions to form a cycloalkanone. Furthermore, except when X and Y are bonded together and comprise five or fewer atoms, over reduction of the 3-indolyl-α keto ester to the 3-indolyl acetic acid ester is not observed.

Thus, the present process is useful in preparing compounds of the Formula I. The compounds of the Formula I are PKC inhibitors and useful in treating diseases implicated by PKC, particularly diabetes mellitus and, more specifically, diabetic complications. The amount of compound of Formula I administered is an amount that is capable of inhibiting PKC activity in mammals. The particular dose of the compound administered according to this invention will, of course, be determined by the particular circumstances surrounding the case, including the compound administered, the route of administration, the particular condition being treated, and similar considerations.

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, N,N-dimethylformamide, palladium on charcoal, tetrahydrofuran, and ethyl acetate are abbreviated M.Pt., NMR, MS, HPLC, DMF, Pd/C, THF, and EtOAc respectively. The terms "NMR" and "MS" indicate that the spectrum was consistent with the desired structure.

PREPARATION 1

1-6 Bisindole hexane

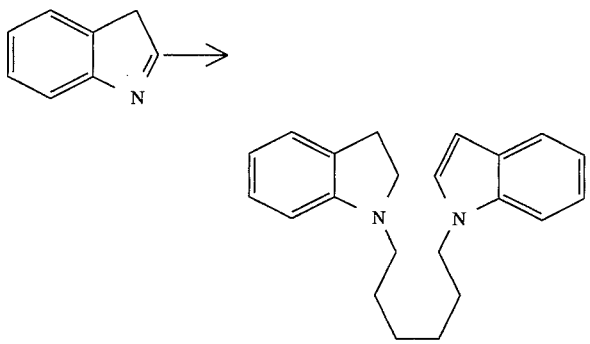

A dry 3 necked flask equipped with reflux condenser was charged with NaH (2.70 g, 68 mmol, 60% dispersion in oil) that was washed with hexane to remove oil. Washed NaH was then suspended in DMF (40 mL) and stirred vigorously at 0° C. To this suspension was added indole (5.3 g, 45 mmol) in DMF (40 mL) over a period of 5 minutes. The resulting mixture was stirred for 1 hour at 0° C. followed by dropwise addition of 1,6 dibromide (3.5 mL, 22.5 mmol) in DMF (40 mL) over a period of 30 minutes. This mixture was then allowed to warm to room temperature and stirred overnight. Excess NaH was destroyed by the addition of excess MeOH. The mixture was then extracted with ether (250 mL×3). The combined organic phase was washed with brine (20 mL) followed by drying over $MgSO_4$ and concentrated to provide crude product that was passed through a short silica column (eluted with 5% ethyl acetate in hexane) to afford pure 1-6-Bis-indole hexane (6.84 g, 96%). MS.

$^1$H NMR (CDl$_3$) δ 7.66 (d,J=10 Hz, 2H, C-2 indole), 7.56–7.03 (m, 6H, indole), 6.50 (d, 2H, C-3 indole), 4.06(t, J=7 Hz 4H, NCH$_2$(CH$_2$)$_4$CH$_2$N), 1.90–1.73 9m, 4H, NCH$_2$CH$_2$(CH$_2$)$_2$CH$_2$CH$_2$N), 1.36–1.26 (m, 4H, N(CH$_2$)CH$_2$CH$_2$(CH$_2$)$_2$N).

PREPARATION 2

1,6 bis (3-Methylglyoxate indole) hexane

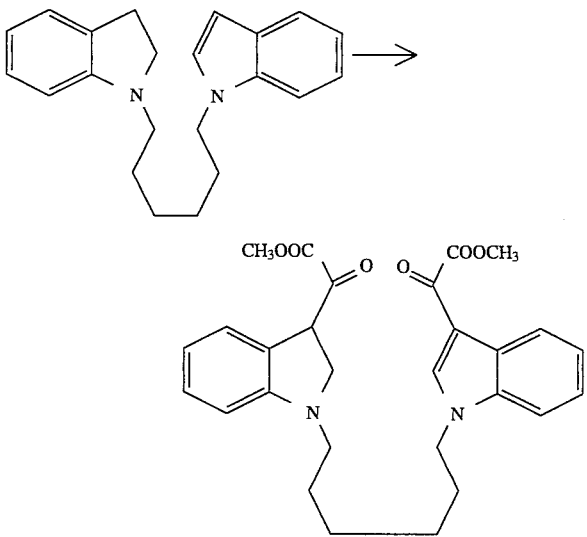

To a stirred solution of 1,6-bis(3-Methylglyoxate indole) hexane (2.00 g, 6.31 mmol) in THF (65 mL) at 0° C. was added oxalyl chloride (1.4 mL, 15.79 mmol) dropwise over a period of 5 minutes. The resulting solution was then stirred for 3 hours when TLC analysis of the reaction mixture indicated consumption of starting material. It was necessary to quench an aliquot of the reaction mixture with MeOH and analyze by TLC (25% ethyl acetate in hexane) to make sure the intermediate mono methoxylated starting material was converted to final product. The mixture was acidified with HCl to pH 3 when the HCl salt of the product precipitated. These precipitate were filtered and washed with hexane. These washed precipitate were then suspended in THF and 1M NaOH was added until pH was ~7 when the suspension turned clear. The resulting solution was extracted with ethyl acetate (50 mL×3), dried over $MgSO_4$ and concentrated under reduced pressure to yield crude product that was purified by passing through a short silica column eluted with 50% ethyl acetate in hexane to yield pure 1,6-bis(3-Methylglyoxate indole) hexane (3.12 g, 80%) . MS.

$^1$H NMR (CDCl$_3$) δ 8.50–8.43 (m, 2H, C-7 indole), 7.40–7.30 (m, 6H, indole), 4.16 (t,J=7 Hz, 4H, NCH$_2$(CH$_2$)$_4$CH$_2$N), 3.96 (s, 6H, COOCH3), 1.96–1.83 (m, 4H, NCH$_2$CH$_2$(CH$_2$)2CH$_2$N), 1.43–1.30 (m, 4H, N(CH$_2$)$_2$CH$_2$CH$_2$(CH$_2$)$_2$N). IR $^v$max 1725 (COOMe str), 1639 (ketone str.).

PREPARATION 3

1,7-Bisindole heptane

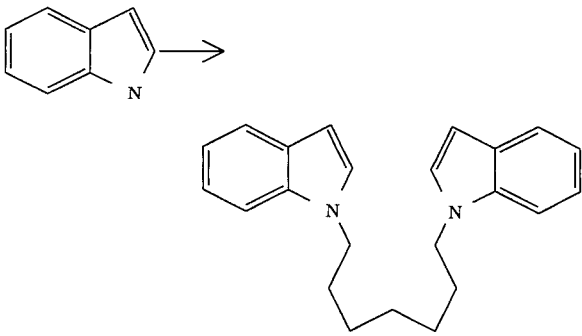

A dry 250 mL round bottom flask with a magnetic stirrer was charged with a 60% dispersion of NaH in oil (4.02 g, 100.60 mmol). Excess oil was then washed using dry hexane (~10 mL) followed by addition of dry DMF (150 mL). The resulting slurry was cooled to 0° C. using icebath followed by dropwise addition of indole (9.06 g, 77.42 mmol) in DMF (50 mL). The reaction mixture was allowed to warm up to the room temperature and stirred for 1 hour. To this mixture was added 1–7 dibromoheptane (10 g, 38.71 mmol) over 5 minutes. The resulting mixture was stirred for additional 24 hours followed by dropwise addition of water (~20 mL) and extraction with ether (50 mL×3). The combined organic phases were washed with brine (50 mL), dried over MgSO4 and concentration under reduced pressure to yield crude product. This crude product was cleaned by passing through a short silica column that was eluted with 10% ethyl acetate in hexane to afford pure 1,7-bisindole heptane (11.5 g, 90%). MS.

$^1$H NMR (CDCl$_3$, 250 MHz) δ 7.83 (d, J=7.50 Hz, 2H, Ar), 7.52–7.14 (m, 8H, Ar), 6.68 (d, J=5.00 Hz, 2H, Ar), 4.18 (t, J= 6.87 Hz, 4H, NCH$_2$(CH$_2$)$_5$CH$_2$N), 2.00–1.82 (m, 4H,

NCH$_2$CH$_2$(CH$_2$)$_3$CH$_2$CH$_2$N), 1.44–1.33 (m, 4H, N(CH$_2$)2CH$_2$CH$_2$CH$_2$(CH$_2$)$_2$N), 1.18–1.00 (m, 2H, N(CH$_2$)$_3$CH$_2$(CH$_2$)

PREPARATION 4

1,7-bis(3-Methylglyoxate indole) heptane

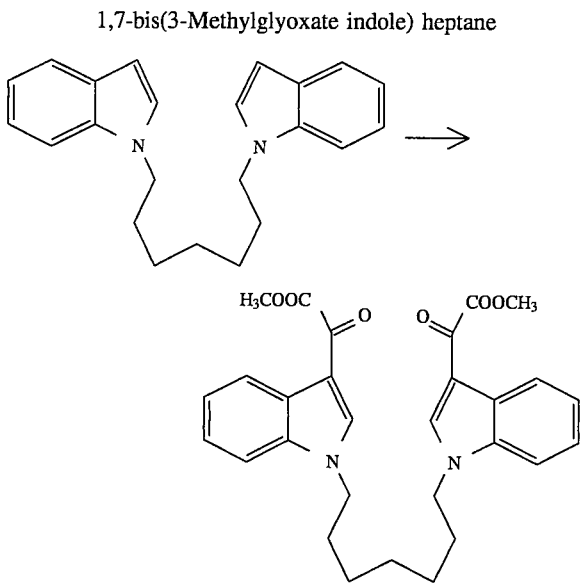

To a stirred solution of bisindole heptane (2 g, 6.31 mmol) in THF (65 mL) was added at 0° C. oxalylchloride (1.4 mL, 15.79 mmol) dropwise over a period of 5 minutes. The mixture was stirred for 3 hours at 0° C. when TLC indicated the complete consumption of starting material. The reaction was then quenched with MeOH (766 μL, 18.93 mmol) and stirred for additional 1 hour. This mixture was acidified to pH 1 with 0.2 N aqueous HCl when the product precipitated out of the solution. These precipitates were filtered and washed with water to completely remove HCl followed by air drying to give pure product (3.12 g, 80%). MS.

$^1$H NMR (CDCl$_3$, 250 MHz) δ 8.48–8.39 (m, 2H, Ar), 8.32 (s, 2H, Ar), 7.36–7.27 (m, 6H, Ar), 4.10 (t, J=8.25 Hz, 4H, NCH$_2$(CH$_2$)$_5$CH$_2$N), 3.92 (s, 6H, COOCH$_3$), 1.93–1.78 (m, 4H, NCH$_2$CH$_2$ (CH$_2$)$_3$CH$_2$CH$_2$N), 1.38–1022 (m, 6H, NCH$_2$CH$_2$ (CH$_2$)$_3$CH$_2$CH$_3$N

EXAMPLE 1

Macrocyclic Diester

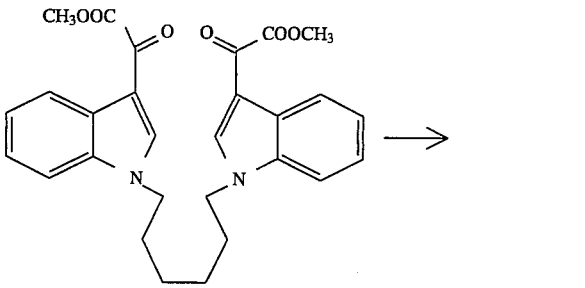

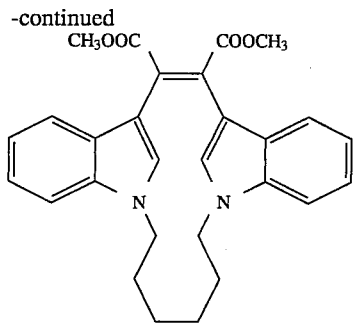

To a stirred slurry of Zn—Cu couple (60 mg) in DME (15 mL) was added TiCl$_3$ (400 mL, 0.4 mmol, 1M solution in 2:1 CH$_2$/Cl$_2$:THF). The resulting mixture was stirred for 10 minutes followed by addition of diketone (53 mg, 0.1 mmol) in DME (10 mL). The mixture was stirred at room temperature for 1 hour when the analysis of the reaction mixture indicated the complete consumption of starting material. The mixture was stirred for another 1 hour followed by quenching the mixture with aqueous NaHCO$_3$ (2 mL) and aqueous EDTA. The mixture was then diluted with ethyl acetate, organic phase separated and aqueous phase extracted with ethyl acetate (10 mL×3). The combine organic phase was dried over MgSO$_4$, concentrated under reduced pressure to afford crude product (48 mg material balance) that was purified by column chromatography using 10% ethyl acetate in hexane to yield pure product (21.8 mg, 48%). MS.

$^1$H NMR (300 MHz, CDl$_3$) δ 7.56–7.50 (m, 2H,C-7 indole), 7.36–7.33 (m, 6H, indole), 6.70 (s, 2H, C-3 indole), 4.03–3.96 (m, 4H, NCH$_2$(CH$_2$)$_4$CH$_2$N), 3.86 (s, 6H, COOH$_3$), 1.90–1.80 (m, 4H, NCH$_2$CH$_2$(CH$_2$)2CH$_2$N), 1.03–0.96 (m, 4H, N(CH$_2$)$_2$CH$_2$CH$_2$(CH$_2$)$_2$N). IR $^v$max 1716 α-β unsat. COOMe str.)

EXAMPLE 2

Macrocyclic Anhydride

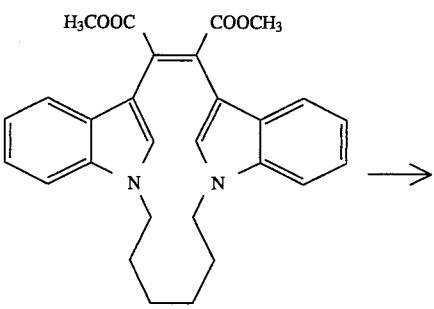

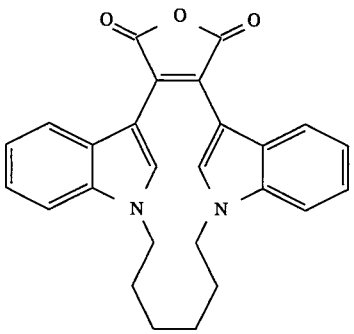

To a stirred solution of bismethyl ester (105 mg, 0.22 mmol) in dioxane (10 mL) and MeOH (10 mL) was added aqueous 5 N NaOH solution (4 mL). The reaction mixture was stirred overnight at 50° C. followed by acifying with concentrated HCl to pH 1. This resulting mixture was then extracted with ethyl acetate (10 mL×4). The combined organic phase, that was deep red in colour, was dried over $MgSO_4$ and concentrated under reduced pressure to yield crude anhydride. This crude anhydride was cleaned by passing through a short silica column that was eluted with ethyl acetate to obtained pure macrocyclic anhydride (66 mg, 73%). MS.

$^1$H NMR ($CDCl_3$, 300 MHz) δ 8.01–8.00 (m, 2H, Ar), 7.38–7.25 (m, 8H, Ar), 4.12–4.08 (m, 4H, $NCH_2(CH_2)_4CH_2N$), 1.95–1.92 (m, 4H, $NCH_2CH_2(CH_2)_2CH_2CH_2N$), 1.19–1.18 (m, $N(CH_2)_2CH_2CH_2(CH_2)_2N$).

EXAMPLE 3

Macrocyclic maleimide

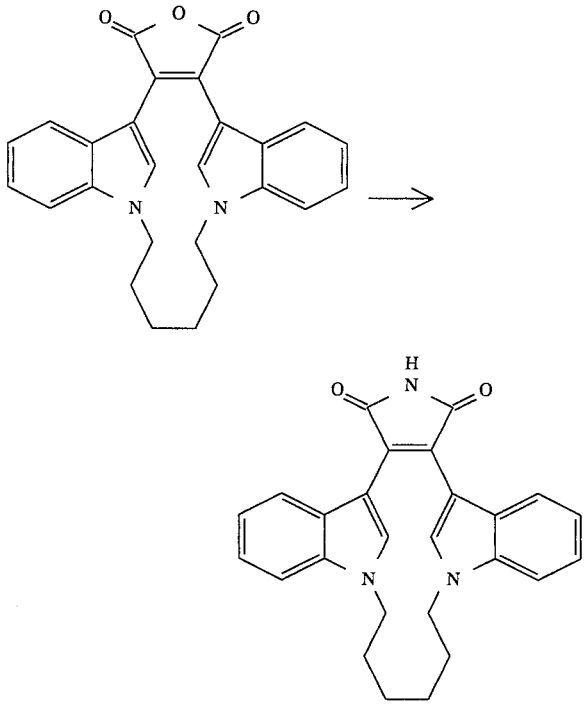

To a stirred solution of Macrocyclic anhydride (66 mg, 0.16 mmol) in dry DMF (15 mL) was added hexamethyldisilazane (340 mL, 1.60 mmol) followed by addition of MeOH (32 mL, 0.8 mmol). The resulting reaction mixture was stirred for 48 hours at 50° C. when the the (25% ethyl acetate in hexane) analysis of reaction mixture indicated the complete consumption of starting material. The reaction mixture was then concentrated under reduced pressure, the residue redissolved in EtOAc (20 mL) that was washed once with water (10 mL) and brine (10 mL). The resulting organic phase was dried over $MgSO_4$ followed by concentration under reduced pressure to yield crude macrocyclic maleimide that was cleaned by passing through a short silica column eluting with ethyl acetate to afford pure maleimide (47 mg, 73%). MS.

$^1$H NMR ($CDCl_3$, 300 MHz) δ 8.00–7.97 (m, 2H, Ar), 7.35–7.10 (m, 8H, Ar), 4.13–3.96 (m, 4H, $NCH_2(CH_2)_4CH_2N$), 2.00–1.86 (m, 2H, $NCH_2CH_2(CH_2)_2CH_2CH_2N$), 1.23–1.06 (m, 2H, $N(CH_2)_2CH_2CH_2(CH_2)_2N$).

$^{13}$C NMR ($CDCl_3$, 75 MHz) δ 170.9, 135.5, 132.8, 130.8, 127.2, 122.3, 121.9, 121.1, 109.9, 103.6, 45.0, 27.7, 23.3.

EXAMPLE 4

7 C Linked Macrocyclic diester

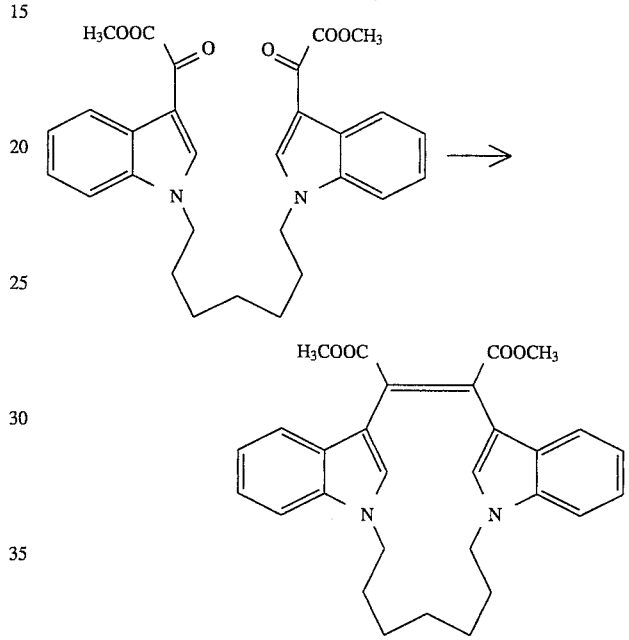

To a stirred slurry to Zn—Cu couple (103 mg, 1.59 mmol) in DME (10 mL) was added 1M solution of $TiCl_3$ (790 μL, 0.79 mmol) in $CH_2Cl_2$ and THF (2:1). The resulting dark coloured solution was stirred for 10 minutes when 1,7-bis(3-Methylglyoxate indole) heptane (100 mg, 0.19 mmol) in DME (10 mL) was added to it all at once. This reaction mixture was then stirred overnight at room temperature. The reaction was stopped by addition of water (2 mL) followed by dilution with ethyl acetate (20 mL). To the resulting mixture was added aqueous sat. $K_2CO_3$ (20 mL) and was extracted with ethyl acetate (20 mL×4). The extract was washed with water (10 mL×2) and brine (10 mL) followed by drying over $MgSO_4$. This dried organic phase was then concentrated under reduced pressure followed by purification by column chromatography on silica gel eluting the column with 10% ethyl acetate in hexane followed by 25% ethyl acetate in hexane to afford the pure seven carbon linked macrocycle (38 mg, 43%).

$^1$H NMR ($CDCl_3$, 250 MHz) δ 7.61–7.53 (m, 2H, Ar), 7.32–7.02 (m, 6H, Ar), 6.75 (s, 2H, Ar), 3.95–3.88 (m, 4H, $NCH_2(CH_2)_5CH_2N$), 3.82 (s, 6H, $COOCH_3$), 1.88–1.72 (m, 4H, $NCH_2CH_2(CH_2)_3CH_2CH_2N$), 1.60–1.44 (m, 6H, $NCH_2CH_2(CH_2)_3CH_2CH_2N$).

We claim:

1. A compound of the Formula:

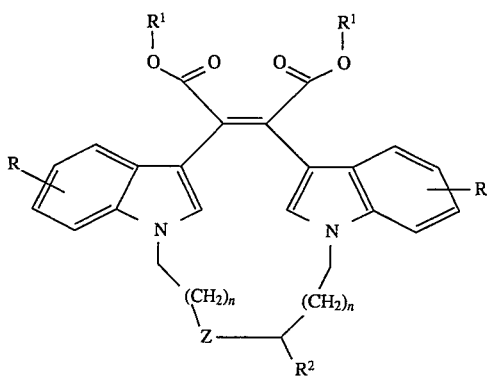

wherein:

Z is —O—, —NR$_3$—, —CONH—, or —NHCO—;

R is independently hydrogen, halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^1$ is a C$_1$–C$_4$ alkyl;

R$^2$ is hydrogen, —(CH$_2$)$_n$C$_1$–C$_4$ alkoxy, —(CH$_2$)$_n$NR$^4$R$^5$, —(CH$_2$)$_n$NH (CF$_3$), —(CH$_2$)$_n$H(CF$_3$) (CH$_3$), —(CH$_2$)$_n$NH(CH$_2$)$_n$aryl, —(CH$_2$)$_n$NH(CH$_2$)$_n$pyridyl, —(CH$_2$)$_n$CONH((CH$_2$)$_m$aryl), —(CH$_2$)$_n$CONH (C$_1$–C$_4$ alkyl), —(CH$_2$)$_n$NHCO(C$_1$–C$_4$ alkyl), —(CH$_2$)$_n$NHCO(CH$_2$)$_n$aryl, —(CH$_2$)$_n$OCONH(C$_1$–C$_4$ alkyl), —(CH$_2$)$_n$OCONH(CH$_2$)$_n$aryl, —(CH$_2$)$_n$NHCOO(alkyl), —(CH$_2$)$_n$NHCOO(benzyl), —(CH$_2$)$_n$NHSO$_2$(C$_1$–C$_4$ alkyl), —(CH$_2$)$_n$NHSO$_2$(CH$_2$)$_n$aryl, —(CH$_2$)$_n$CN, —(CH$_2$)$_n$SO$_2$(NR$^4$R$^5$), —(CH$_2$)$_n$SO$_2$(C$_1$–C$_4$ alkyl), or —(CH$_2$)$_n$SO(C$_1$–C$_4$ alkyl);

R$^3$ is hydrogen, (CH$_2$)$_n$aryl or C$_1$–C$_4$ alkyl;

R$^4$ and R$^5$ are independently hydrogen, methyl, phenyl, benzyl, or combine to the nitrogen to which they are bonded to form a saturated or unsaturated 5 or 6 membered ring; and n is independently 1, 2 or 3.

2. A compound of claim 1, wherein:

R is hydrogen;

R$^2$ is —(CH$_2$)$_n$NR$^4$R$^5$, —(CH$_2$)$_n$NH(CF$_3$), or —(CH$_2$)$_n$N(CF$_3$)(CH$_3$);

R$^4$ and R$^5$ are independently hydrogen or methyl; and n is independently 1 or 2.

3. A compound of claim 2, wherein R$^2$ is —(CH$_2$)NCH$_3$CH$_3$.

4. A compound of claim 3, wherein n is 1.

* * * * *

UNITED STATES PATENT AND TRADEMARK OFFICE
CERTIFICATE OF CORRECTION

PATENT NO. : 5,559,228
DATED : Sept. 24, 1996
INVENTOR(S) : James R. Gillig, et al It is certified that error appears in the above-indentified patent and that said Letters Patent is hereby corrected as shown below:

Column 10, line 36 in structure is blank, should read --H (directly under the N)--

Column 11, line 3 reads ..."N(CH$_2$)$_3$CH$_2$(CH$_2$)"... should read -- N(CH$_2$)$_3$CH$_2$(CH$_2$)$_3$N).--

Column 11, line 47 reads ..."1022"... should read --1.22--

Column 12, line 20 reads ..."the analysis"... should read --tlc analysis--

Col. 13, line 5, reads ..."the the (25%"... should read --the tlc (25%--

Column 15, line 25 reads ..."(CH$_2$)$_n$H(CF$_3$)"... should read --(CH$_2$)$_n$N(CF$_3$)--

Signed and Sealed this

Fourth Day of November, 1997

Attest:

BRUCE LEHMAN

Attesting Officer

Commissioner of Patents and Trademarks